United States Patent
Lemer

(10) Patent No.: US 8,445,093 B2
(45) Date of Patent: May 21, 2013

(54) STERILE COVER FOR A WIND SCREEN MADE OF RADIOPROTECTIVE MATERIAL

(75) Inventor: Pierre-Marie Lemer, Nantes (FR)

(73) Assignee: Lemer Protection Anti-X par Abreviation Societe Lemer Pax, Carquefou (FR)

( * ) Notice: Subject to any disclaimer, the term of this patent is extended or adjusted under 35 U.S.C. 154(b) by 534 days.

(21) Appl. No.: 12/599,397

(22) PCT Filed: May 5, 2008

(86) PCT No.: PCT/FR2008/050787
§ 371 (c)(1),
(2), (4) Date: Jan. 27, 2010

(87) PCT Pub. No.: WO2008/148991
PCT Pub. Date: Dec. 11, 2008

(65) Prior Publication Data
US 2010/0304060 A1  Dec. 2, 2010

(30) Foreign Application Priority Data
May 9, 2007  (FR) ...................................... 07 03316

(51) Int. Cl.
*B32B 3/24* (2006.01)
*A61B 19/02* (2006.01)

(52) U.S. Cl.
USPC ......................................... 428/131; 128/849

(58) Field of Classification Search
USPC .......................................... 428/131; 128/849
See application file for complete search history.

(56) References Cited

U.S. PATENT DOCUMENTS

| 7,112,811 B2 * | 9/2006 | Lemer | ........................ 250/515.1 |
| 2002/0069882 A1 * | 6/2002 | Sklar | ............................. 128/849 |
| 2005/0173658 A1 | 8/2005 | Lemer | |
| 2006/0124871 A1 | 6/2006 | Ballsieper | |

FOREIGN PATENT DOCUMENTS

| WO | WO 03/088267 A1 | 10/2003 |
| WO | WO 2004/107979 A1 | 12/2004 |

OTHER PUBLICATIONS

International Search Report, dated Apr. 29, 2009, from corresponding PCT/FR2008/050787.

* cited by examiner

*Primary Examiner* — William P Watkins, III
(74) *Attorney, Agent, or Firm* — Young & Thompson

(57) ABSTRACT

A sterile screen cover made of radioprotective material has an L-shaped horizontal section, including a front wall associated with a side wall. The front wall has two orifices through which the arms of the operator can pass, a first orifice being located close to the angle of the screen, the second being located on the free edge of the front wall. The sterile cover is a single part that includes at least one internal "panel" and one "external panel" joined together by a joining region, the panels intended to cover, respectively, at least the internal and external faces of the front wall and at least part of the height of its free edge. The joining region has an indentation shaped to match the border of the second passage orifice; these inner and outer panels are each provided with an opening intended to be placed in front of the first passage orifice.

16 Claims, 4 Drawing Sheets

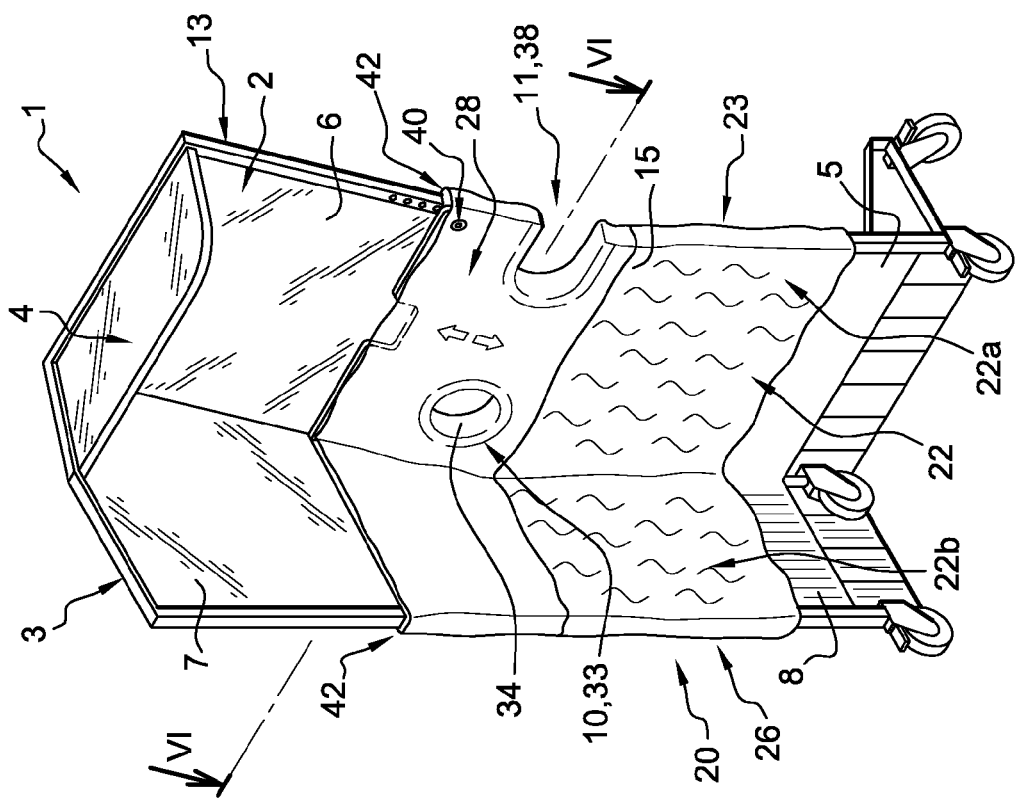
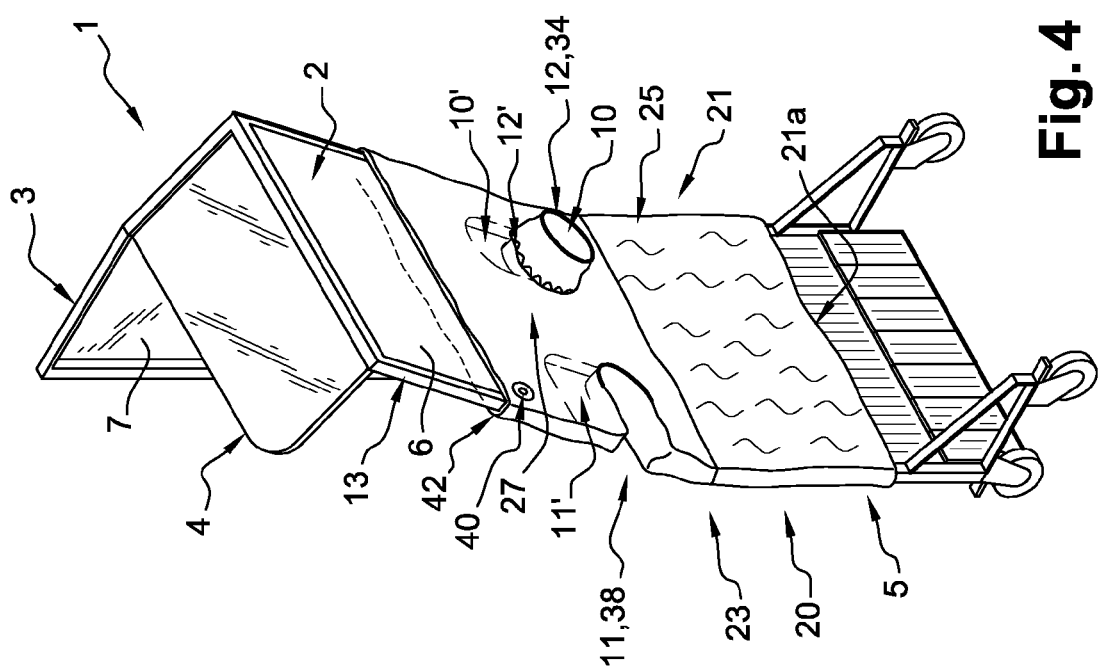

STERILE COVER FOR A WIND SCREEN MADE OF RADIOPROTECTIVE MATERIAL

The present invention relates to a sterile cover for a radioprotective screen adapted to ensure protection of an operator against ionizing radiation of the X-ray type or the like.

Certain medical procedures require the use of injectable products that emit ionizing radiation (it is notably the case for operations of catheterization or pacemaker implantation, but also for certain vascular, neurological and urological examination procedures), or implement directly ionizing radiation for purpose of diagnoses or treatments, for example for the techniques of atrial fibrillation in the field of electrophysiology.

During such procedures, the operator (technician, physician, surgeon or the like) must be protected against the radiation to which the patient is subjected.

For that purpose, the operator may wear garments of the smock, chasuble or apron type, made of radioprotective material. However, optimum working conditions cannot be obtained with such protective garments, in particular due to their heavy weight and the heavy sweating they cause.

To ensure protection against the dangers of ionizing radiation, an interesting variant consists in performing the medical procedure from behind a shield or a screen comprised of panels made of radioprotective material.

Accordingly, the working conditions, without heavy weight garment, allow a more accurate and more efficient procedure, with still optimum security conditions.

For most of the procedures, a sterile plastic film, forming a cover, is added-on to cover the different faces of the screen, so that the procedure is performed in satisfactory sanitary conditions; such sterile cover is replaced by a new one before each procedure.

This type of sterile cover makes it possible to avoid infectious contamination of patients, especially through transfer and dispersion of bacterial germs or virus that would be present on the screen used during the procedure.

A structure of radioprotective screen that is particularly efficient and interesting is described in WO-03/088267.

The corresponding screen is made up of a front wall associated with a side wall extending perpendicularly or substantially perpendicularly from one of the sides of said front wall; these two walls comprising transparent panels over at least part of their height. The upper part of the front wall is tilted forward, overhanging, to allow the operator to come closer to the area where the procedure is performed; this front wall is also provided with two orifices for the passage of the arms of the operator:—a first passage orifice is arranged in the vicinity of the angle formed with the side wall, and—a second passage orifice, which is laterally open, is located at the free edge thereof, thus having the general form of a horizontally oriented circular arc or U-shaped indentation.

Such radioprotective screen structure offers, on the one hand, a good visibility for the operator, and on the other hand, a great comfort regarding the positioning thereof within the framework of the procedure.

However, the current sterile covers are not adapted to this form of screen. Furthermore, they are comprised of several parts that have to be attached together at the time of application on the screen, which requires the cooperation of several persons, so that this operation is not very simple and not very fast. Moreover, according to the structure thereof, the screen is not always efficiently covered.

For these reasons, the applicant has developed a new sterile cover for radioprotective-screen of the type described in WO-03/088267, the structure of which allows a simple, fast and efficient fitting, possibly by a single person.

Once applied, such sterile equipment is perfectly held onto the screen, with a limited risk of falling down; such cover also ensures an efficient covering of the different parts to be protected (in particular the arm passage orifices).

In this case, the sterile cover according to the invention is made up of a single part, which comprises two panels, one being called the "inner panel" and the other being called the "outer panel", which panels are shaped so as to cover at least the inner and outer faces of the front wall of the screen, respectively, over at least part of their height extending below and above the associated arm passage orifices. These inner and outer panels are connected together by a junction region shaped so as to match at least part of the height of the free edge of the front wall, said junction region comprising an indentation shaped so as to match the edge of the laterally open passage orifice; and these inner and outer panels are each provided with an opening intended to be placed on either side of the other passage orifice, the opening of one of said panels being provided with one flexible tubular element forming a kind of cuff, said cuff being intended to be passed through said opposite orifice, so as to cover the edge thereof and to guarantee its asepsis.

According to a supplementary characteristic, the inner and/or outer panels are advantageously extended by one or more panels intended to cover the inner and/or outer faces of the side wall.

According to another characteristic of the invention, for a radioprotective screen whereof, the first passage orifice is extended forwardly by a protective sleeve made of radioprotective material, the opening of the inner panel is extended by a flexible cuff whereof the length is adapted to cover—the inner surface of said protective sleeve, and also—at least part of the length of the outer surface by being folded over. Advantageously, the free end of the cuff of the inner panel is provided with a resilient member, the latter being arranged so as to tend to reduce the diameter thereof and being intended to form a kind of tightening strap adapted to tighten around the outer surface of the protective sleeve (after being passed through said sleeve, and outwardly folded over itself); furthermore, this cuff of the inner panel may be covered with a sheath-shaped removable element whereof one end is closed, said sheath being intended to facilitate the passage operation of said cuff through the protective sleeve and being intended to be removed after said passage operation.

Still in this case, the opening of the outer panel is also advantageously extended by a flexible cuff, the latter being intended to cover at least part of the length of the outer surface of the protective sleeve.

On the other hand, in a particularly interesting manner, the sterile cover comprises—an upper band made of transparent plastic material, and—a portion made of surgical-type absorbent non-woven material, corresponding to a lower band of said cover and/or to the cuff(s) equipping the inner and/or outer panels, and/or to the junction region between said panels; the adjacent edges between the transparent plastic material and said absorbent material are connected together by one or more seams.

Furthermore, such cover advantageously comprises means for attaching it to the screen; preferably, these attaching means consist in suction pads judiciously distributed over the upper edge of the cover. Additionally or as an alternative, these attaching means can also take the form of adhesive-material strips arranged over at least part of the length of the cover's upper edge and/or over at least part of the height of at least one of the end edges thereof.

The invention will be further illustrated, without being in any way limited, by the following description of a particular embodiment, given only by way of example and shown in the attached drawings, in which:

FIG. 4 shows a perspective front view of the radioprotective screen of FIG. 1, now equipped with the sterile cover of FIGS. 2 and 3;

Figure 6:
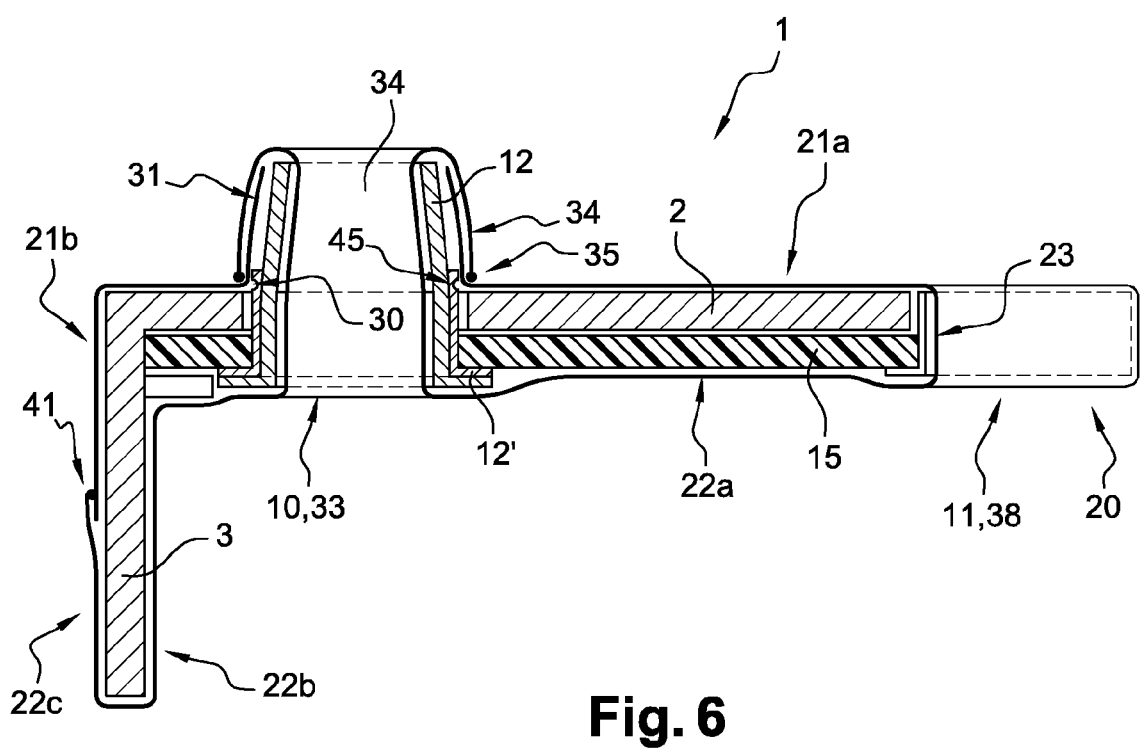

FIG. 5 corresponds to a perspective rear view of the screen of FIG. 4;

FIG. 6 is a sectional view taken along VI-VI of FIG. 5, i.e. in a horizontal plane passing through the screen orifices that permit the passage of the operator's arms, so as to schematically show the arrangement of the sterile cover in position.

Figure 1:
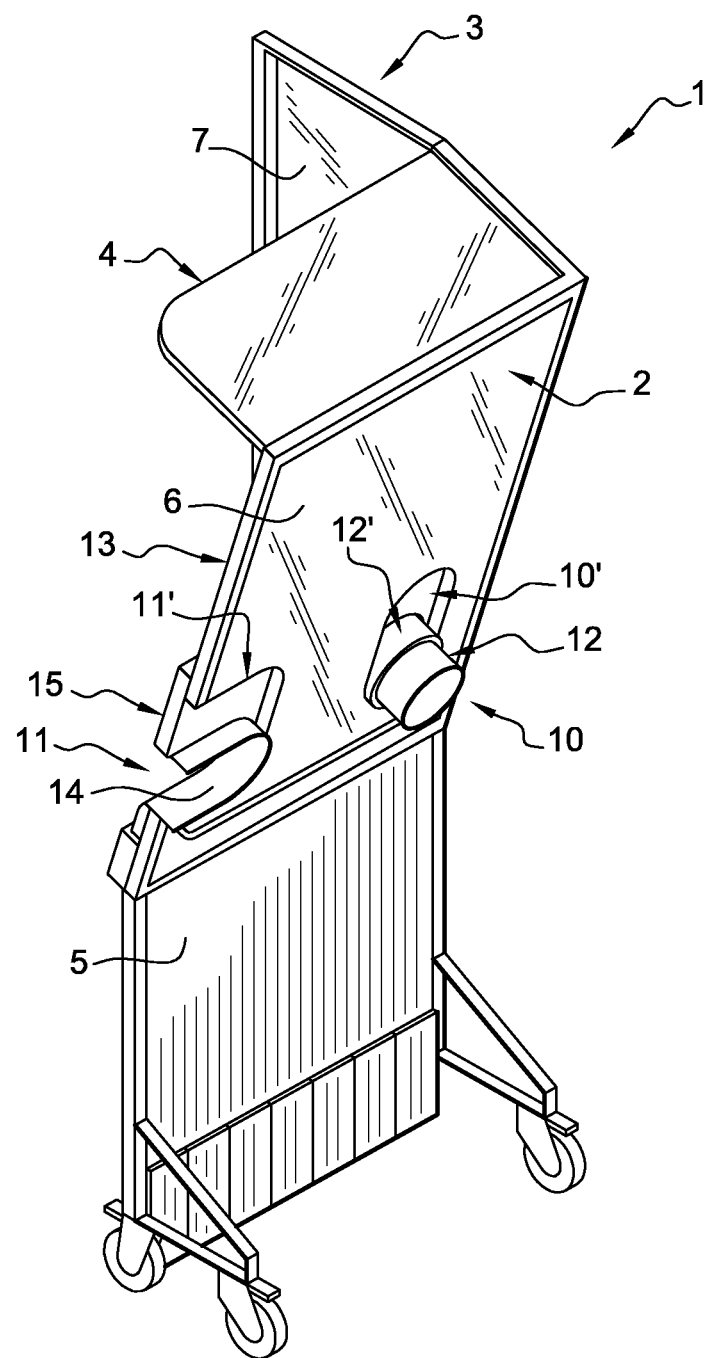
FIG. 1 is an overall perspective front view of a radioprotective screen intended to be partially covered with the sterile cover according to the invention.

The radioprotective screen intended to be covered by the sterile cover according to the invention is described in WO-A-03/088267 and corresponds to the object of FIG. 1.

The radioprotective screen 1 mainly comprises a front wall 2 connected to a vertical side wall 3, which is arranged perpendicularly or substantially perpendicularly to it. An additional wall 4, acting as a ceiling, is herein advantageously provided between the upper flanges of the above-mentioned front 2 and side 3 walls.

This kind of screen, intended to protect an operator against ionizing radiation emissions, consists of rigid plates made of a suitable radioprotective material.

The different plates can be carried by a metallic body structure, for example made of aluminium, which integrates a shield that allows continuity of the radioprotection at every junction. The structure can also be fully or partially made by moulding of a radioprotective material.

In this case, the front wall 2 comprises a lower portion 5 made up of a vertical opaque plate, and an upper portion 6 made up of a transparent plate.

This transparent plate 6 is provided tilted forward, i.e. toward the operative field. Such tilting allows the operator to lean forward when performing the procedure, and thus to come closer to the operative area, especially to have a better visibility and a greater comfort.

The side wall 3 extends vertically on the side. It also comprises a transparent upper plate 7 and an opaque lower plate 8 (shown only in FIG. 5). The transparent plate 7 aims to offer a side visibility to the operator, in particular to watch over the patient or to have visual access to the surrounding instruments.

The side wall 3 matches the dihedral shape of the front wall 2; thus, the transparent panel 7 has a substantially trapezoidal general shape.

The general dimensions of the screen are adapted to permit accommodation of operators of very different sizes.

For example, the front wall 2 and the side wall 3 may be about 2 m high.

The inner panel 5 of the front wall 2 extends preferably up to a level which corresponds to that of the operation table; by way of information, this inner panel may extend over a height comprised between 60 cm and 100 cm, preferably close to 80 cm. The transparent upper panel 6 extends preferably from the level of the operation table, i.e. between about 80 cm from the floor and a height of the order of 2 m.

The transparent upper plate 6 of the front wall 1 is also provided with two orifices 10 and 11 for the passage of the operator's arms, to allow the latter to perform a procedure on the patient.

One of the orifices 10 (referred to as the "first orifice") is generally circular in shape. The orifice 10 is located on the side and in the vicinity of the angle formed by the front 2 and side 3 walls; it is herein adapted for the passage of the left arm of the operator.

To increase the protection of the operator, the orifice 10 is extended by a protective sleeve 12 (for example, iris-shaped) mounted on an adapted tubular support 12'. The protective sleeve 12 protrudes forward, at the place where the patient will be during the procedure performed by the practitioner.

The other orifice 11 (referred to as the "second orifice"), herein intended to receive the right arm of the operator, is arranged at the free edge 13 of the front wall 2, i.e. at the edge opposite to the side wall 3. The orifice 11 is laterally open, and has thus the general form of a horizontally oriented circular arc or U-shaped indentation. The orifice 11 is herein advantageously equipped with a removable ring 14.

This orifice 11 permits the operator to easily insert and extract his arm, and thus to keep a great freedom of movement.

Particular structural means are provided to permit vertical displacement of the orifices 10 and 11 over the height of the transparent plate 6, in order to allow adaptation of their level to the size of the operator. Accordingly, these orifices 10 and 11 are arranged in the transparent plate 6, and also in a backing panel 15 provided inside the screen 1.

This inner backing panel 15, which comprises the above-mentioned protective sleeve 12 and ring 14, is provided moveable parallel to said transparent plate 6, guided by side rails (not shown); the position thereof is, for example, set by means of an index cooperating with an anchoring finger (both not shown).

The transparent plate 6 comprises oblong openings 10' and 11', which are oversized with respect to the above-mentioned orifices 10 and 11, and whereof the dimensions, forms and positions are adapted to the stroke of the backing plate 15 (and especially of the associated sleeve 12 and ring 14).

Figure 2:
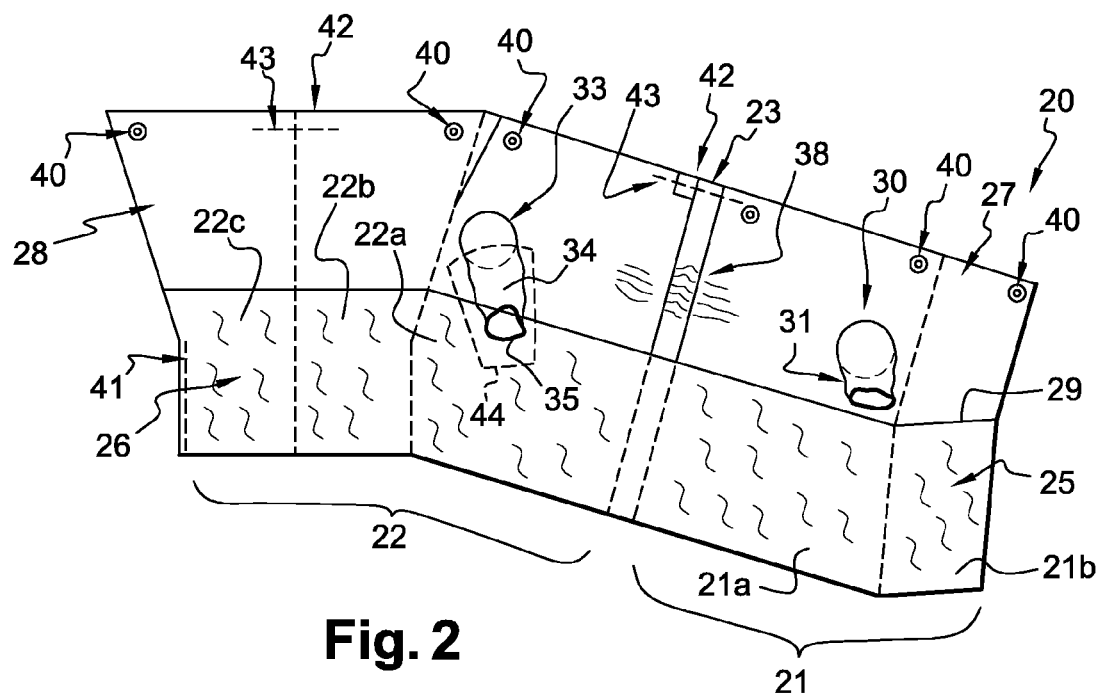
FIG. 2 is a schematic, approximately developed, side view of the outer face of a sterile cover according to the invention, adapted to cover the screen of FIG. 1.
Figure 3:
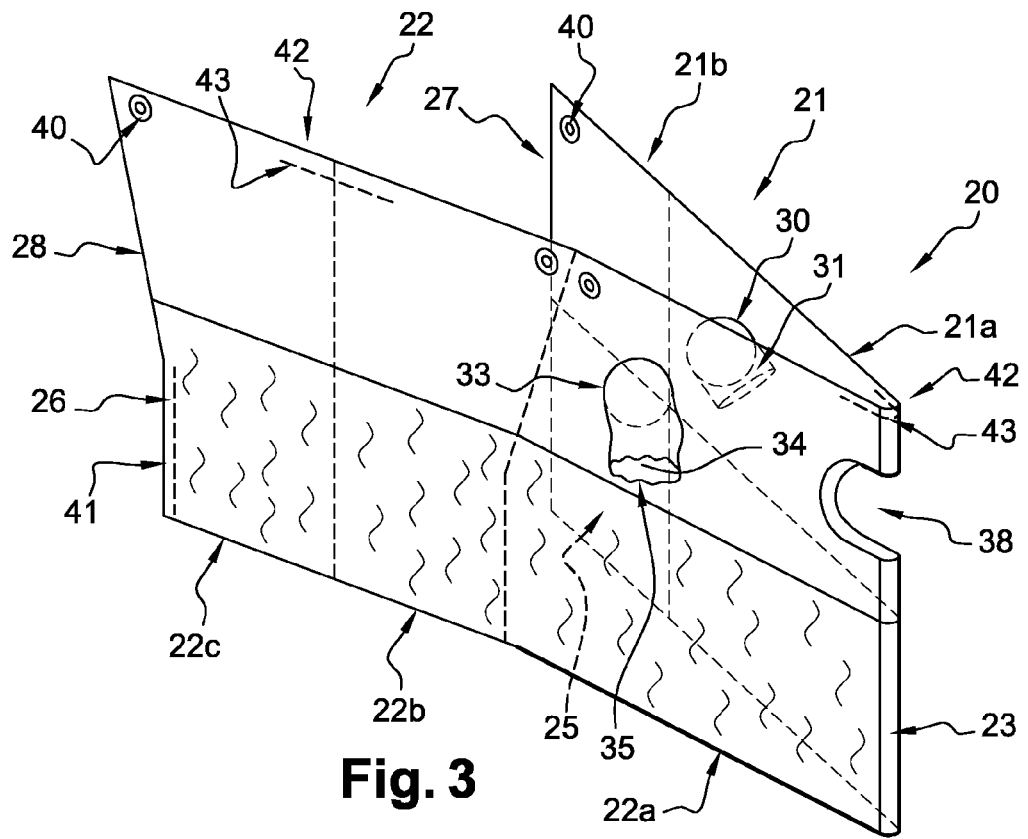
FIG. 3 is an overall perspective view of the cover of FIG. 2, partially folded around the junction region between the outer panel and the inner panel.

The sterile cover 20 according to the invention, shown in a flat condition in FIG. 2, and in a partially bulk condition in FIG. 3, is adapted to partially cover the radioprotective screen 1 described above in relation with FIG. 1.

The sterile cover 20, in a flat condition (FIG. 2), has the form of a longitudinal band or membrane, mainly made up of two parts 21 and 22 whereof the opposite edges are connected by a transverse band 23 forming a transverse junction region. By way of information, the dimensions of the parts 21 and 22 of the cover 20 are about 100 cm×100 cm and 150 cm×150 cm, respectively. Generally, they are adapted to the dimensions of the radioprotective screen 1.

The cover 20 is made single-piece through assembling of two flexible materials adapted to medical use.

More precisely, the two parts 21 and 22 each comprise:

a "lower" band 25 or 26, made of surgical-type absorbent non-woven material, for example based on polypropylene 40 g/m$^2$, and a transparent "upper" band 27 or 28, consisting in a flexible transparent plastic film, such as, for example, about 70 μm thick transparent polypropylene.

The "lower" band 25, 26 extends over the whole length of the cover 20, just as the "upper" band 27, 28; these two longitudinal bands are separated by a junction line 29.

As for the junction region 23, it is made of surgical-type absorbent non-woven material similar to that used for the lower bands 25 and 26 of the panels 21 and 22.

The bands of absorbent material 23, 25, 26 and the bands of transparent plastic material 27 and 28 are attached together, at their opposite edges, by connection means of the seam type.

More precisely, the first part 21 (located on the right in FIG. 2) is also made up of two panels 21a and 21b, intended to cover the front face of the front wall 2 of the screen and a portion of the front face of the side wall 3 thereof, respectively. Said panel 21a, herein after referred to as the "outer panel" to simplify the description, has a width corresponding to that of the front wall 2 of the screen 1. The outer panel 21a comprises, at the transparent upper band 27, a circular opening 30 extended by a cuff 31, made of flexible non-woven material (of the same type as that used for the lower bands 25 and 26).

The width of the other panel 21b of this first part 21 corresponds to a part the width of the side wall 3, and in this case a little more than half this width.

The second part 22 of the sterile cover 20 (located on the left of the junction region 23 in FIG. 2) is made up of three panels 22a, 22b and 22c intended to cover the inner face of the front wall 2 (in other words, its rear face), the inner face of the side face 3 and a portion of the outer face of said side wall 3, respectively.

The width of the panel 22a corresponds to that of the front wall 2. A circular opening 33 is provided in the transparent band 28 thereof; the opening 33 is arranged symmetrically to the opening 30 of the outer panel 21a with respect to the junction region 23.

The opening 33 is also extended by a cuff 34; the free edge of the latter is equipped with a resilient member 35 adapted to tend to reduce the diameter thereof.

It is still to be noted that the length of the cuff 34 is greater than that of the cuff 31 of the outer panel 21a.

The junction region 23 is intended to match the free edge 13 of the front wall 2. Accordingly, the junction region 23 has a width corresponding approximately to the thickness of this front wall 2.

As can be seen in particular in FIG. 3, this region 23 comprises a segment 38 forming a kind of indentation, having a generally horizontally-oriented U shape, and arranged at a level located between the two arm passage openings 30 and 33 provided in the panels 21a and 22a. The shape and dimensions of the indentation 38 are adapted to match, the closest possible, the inner edge of the arm passage orifice 11, being in the form of an open indentation, of the screen 1.

To allow the mounting thereof to the screen 1, the cover 20 is also provided with several suction pads 40 arranged over the length of the upper edge thereof, on the side oriented toward the screen. Moreover, an adhesive strip 41 is arranged on the lower portion of the free side edge of the panel 26, still on the side oriented toward the screen.

The adhesive used is advantageously of the "repositionable" type.

The shape of the junction line between the panels 22a and 22b, and between the panels 21a and 21b, is adapted to the inclination of the transparent panel 6 of the screen.

Moreover, the shapes and dimensions of the different panels making up the cover 20 are generally provided so that such cover 20 can be adapted to a range of screens having slight size variations. To optimise such adaptation, resilient tightening regions 42 are arranged at the upper ends of the cover's bands intended to cover the free side edges of the screen; these tightening regions 42 are obtained by means of resilient bands 43 suitably sewn to the transparent panels 27 and 28, to exert a longitudinal tensile strength to the material.

Thus, the cover 20 consists of a band of material intended to wrap part of the height of the screen 1, on either side of the arm passage orifices 10, 11, i.e. above and below said orifices. The screen "wrap" height may be comprised between 80 and 120 cm; it is advantageously of the order of 100 cm.

The upper part of the cover 20 (made up of the transparent panels 27 and 28), due to the transparency thereof, offers the practitioner visual access to the operative field; preferably, this upper part 27, 28 does not extend too high, so as not to hinder the visual access to the control equipments located upright (nevertheless, the transparent plastic film is an element that slightly "disrupt" the visibility).

The lower non-woven part of the cover 20 (made up of the panels 25 and 26) is there to remind the product technicality; it has a liquid-absorbing capacity liable to present an interest in the present invention.

The setting of the cover 20 to the screen 1 is made in a very simple and fast manner, as described hereinafter in relation with FIGS. 4 to 6.

Initially, the cover 20 is packed in sterile condition inside a hermetically sealed pouch, in which it is suitably folded to reduce the bulk thereof.

Within this pack, the cuff 34 of the inner panel 22a is advantageously accommodated in a sheath 44 illustrated in dotted line in FIG. 2.

This sheath 44, one end of which is closed, is intended to facilitate the "sterile" installation of the cover to the screen. For the setting, the operator has firstly to take the cover out of its pouch, then to unfold it; for this purpose, it is advisable that all the usual precautions are taken not to contaminate the equipment (wearing of gloves, smock, etc.).

The operator then suitably positions the different panels 21a, 22a, 22b, 21b and 22c of the cover 20 against the various faces of the screen 1, by positioning the junction region 23 opposite the free edge 13 of the front wall 2 and by making the free vertical edges of said end panels 21b and 22c partially overlap against the outer face of the side wall 3.

The corresponding suitable positioning is obtained by placing the orifices 30 and 33 of the cover opposite the orifice 10 of the screen, on the inner and outer sides of the front wall 2, respectively, and by using the suction pads 40.

The cuff 31 of the cover then covers the outer surface of the tubular support 12' and of the radioprotective sleeve 12; the operator then passes the cuff 34, from inside to outside, through the orifice 10, such operation being facilitated by the above-mentioned sheath 44.

Once the operation performed, the operator removes the sheath 44; he/she folds over the resilient free end 35 of the cuff 34 around the sleeve 12, toward the front wall 2, so that the cuff also covers the peripheral outer surface of said protective sleeve 12 and of its associated cuff 31 (as can be seen in FIG. 6); the resilient free end 35 of the cuff 34 is then inserted into an annular groove 45 provided in the tubular support 12' (see also FIG. 6).

It is to be noted that the cuff 34 is accordingly efficiently held through the passage orifice 10 and is especially able to resist to insertion and extraction movements of the practitioner's arms through said orifice 10.

At the same time, the operator has to make sure that the junction region 23 correctly matches the free edge 13 of the front end 2, and that the indentation 38 thereof is accommodated in the arm-passage side orifice 11.

Generally, in practice, it proves interesting:
to firstly cover the outer face of the screen front end 2, by fastening the upper edge of the panel 21a by means of the associated suction pads 40,
to position the side panel 21b against the outer face of the side wall 3 by using the suction pads 40 thereof, to complete the covering operation by successively sticking the panels 22a, 22b and 22c with the use of their own suction pads 40.

The adhesive strip 41 is finally used to attach the lower part of the panel 22c to the outer face of the panel 21b.

The suction pads 40 being repositionable, the operator is able to adjust the position of the cover 20 so that the latter matches at best the screen.

Once the cover 20 suitably applied (as shown in FIGS. 4 to 6), the practitioner can perform the considered medical procedure on the patient.

It is to be noted that the transparent bands 27 and 28 are arranged opposite the transparent panels 6 and 7 of the screen 1 (over part of their height), which preserves an efficient visual comfort while ensuring optimum sanitary conditions for the patient. Likewise, the arm-passage orifices 10 and 11 are protected by the sterile cuff 34 and the indentation 38, respectively, which further reduces infectious risk for the patient.

This type of sterile cover is single-use and, once the medical procedure completed, it is easy to separate the cover from the screen by simple pulling efforts.

Generally, it is to be understood that the setting of such sterile cover is particularly simple and fast and can be carried out by a single operator. Such a cover has also the interest that it ensures an optimum covering of the regions of the radioprotective screen liable to be in contact with the hands or the arms of the practitioner.

The invention claimed is:

1. A sterile cover intended to cover at least part of the height of a screen (1) made of radioprotective material ensuring protection of an operator against the ionizing radiation emissions of the X-ray type, wherein said screen (1), of the type having an L-shaped horizontal cross-section, is made up of a front wall (2) associated with a side wall (3) extending perpendicularly or substantially perpendicularly from said front wall (2), wherein said front wall (2) is provided with two orifices (10, 11) for the passage of the arms of said operator, a first passage orifice (10) being arranged in the vicinity of the angle formed by said front (2) and side (3) walls, a second passage orifice (11) being located at the free edge (13) of said front wall (2) and being laterally open, thus having the general form of a horizontally oriented circular arc or U-shaped indentation, characterized in that said sterile cover (20) is in the form of a single part, which comprises at least two panels, one being referred to as the "inner panel" (22a) and the other being referred to as the "outer panel" (21a), shaped so as to cover at least the inner and outer faces of said front wall (2), respectively, over at least part of their height extending below and above said arm passage orifices (10, 11), wherein said inner (22a) and outer (21a) panels are connected by a junction region (23) shaped so as to match at least part of the height of the free edge (13) of said front wall (2), said junction region (23) comprising an indentation (38) shaped so as to match the edge of said second passage orifice (11), and wherein said inner (22a) and outer (21a) panels are each provided with an opening (30, 33) intended to be placed on either side of said first passage orifice (10), the opening (30, 33) of at least one of said panels (21a, 22a) being provided with a flexible tubular element (34) forming a kind of cuff, said cuff (34) being intended to be passed through said first orifice (10), so as to cover the edge thereof and to guarantee asepsis of said orifice (10).

2. A sterile cover according to claim 1, characterized in that the inner (22a) and/or outer (21a) panels are extended by one or several panels (22b, 22c; 21b) intended to cover the inner and/or outer faces of the side wall (3).

3. A sterile cover according to claim 1, for a radioprotective screen (1), the first passage orifice (10) of which is extended forward by a protective sleeve (12) made of radioprotective material, characterized in that the opening (33) of the inner panel (22a) is extended by a flexible cuff (34), the length of which is adapted to cover the inner surface of said protective sleeve (12), and also at least part of the length of the outer surface thereof.

4. A sterile cover according to claim 3, characterized in that the free end (35) of the cuff (34) of the inner panel (22a) is provided with an elastic member, the latter being arranged so as to tend to reduce the diameter thereof and being intended to form a kind of tightening strap adapted to tighten around the outer surface of the protective sleeve (12) or an associated sleeve support (12').

5. A sterile cover according to claim 3, characterized in that the opening (30) of the outer panel (21a) is also extended by a flexible cuff (31), the latter being intended to cover at least part of the length of the outer surface of the protective sleeve (12).

6. A sterile cover according to claim 3, characterized in that the cuff (34) of the inner panel (22a) is covered with a sheath-shaped removable element (44), one end of which is closed, said sheath (44) being intended to facilitate the passage operation of said cuff (34) through the protective sleeve (12) and being intended to be removed after said passage operation.

7. A sterile cover according to claim 1, characterized in that it comprises an upper band (27, 28) made of transparent plastic material.

8. A sterile cover according claim 7, characterized in that it comprises a part made of surgical-type absorbent non-woven material, corresponding to a lower band (25, 26) of said cover (20), and/or to the cuff(s) (31, 34) equipping the inner (22a) and/or outer (21a) panels, and/or to the junction region (23) between said panels (21a, 22a), the adjacent edges between the transparent plastic material and said absorbent material are connected together by one or several seams.

9. A sterile cover according to claim 1, characterized in that it comprises means (40, 41) for attaching it to the screen (1).

10. A sterile cover according to claim 9, characterized in that the attaching means comprise suction pads (40) distributed over the length of its upper edge.

11. A sterile cover according to claim 2, for a radioprotective screen (1), the first passage orifice (10) of which is extended forward by a protective sleeve (12) made of radioprotective material, characterized in that the opening (33) of the inner panel (22a) is extended by a flexible cuff (34), the length of which is adapted to cover the inner surface of said protective sleeve (12), and also at least part of the length of the outer surface thereof.

12. A sterile cover according to claim 4, characterized in that the opening (30) of the outer panel (21a) is also extended by a flexible cuff (31), the latter being intended to cover at least part of the length of the outer surface of the protective sleeve (12).

13. A sterile cover according to claim 11, characterized in that the opening (30) of the outer panel (21a) is also extended by a flexible cuff (31), the latter being intended to cover at least part of the length of the outer surface of the protective sleeve (12).

14. A sterile cover according to claim 4, characterized in that the cuff (34) of the inner panel (22a) is covered with a sheath-shaped removable element (44), one end of which is closed, said sheath (44) being intended to facilitate the passage operation of said cuff (34) through the protective sleeve (12) and being intended to be removed after said passage operation.

15. A sterile cover according to claim 5, characterized in that the cuff (34) of the inner panel (22*a*) is covered with a sheath-shaped removable element (44), one end of which is closed, said sheath (44) being intended to facilitate the passage operation of said cuff (34) through the protective sleeve (12) and being intended to be removed after said passage operation.

16. A sterile cover according to claim 13, characterized in that the cuff (34) of the inner panel (22*a*) is covered with a sheath-shaped removable element (44), one end of which is closed, said sheath (44) being intended to facilitate the passage operation of said cuff (34) through the protective sleeve (12) and being intended to be removed after said passage operation.

* * * * *

UNITED STATES PATENT AND TRADEMARK OFFICE
CERTIFICATE OF CORRECTION

PATENT NO.       : 8,445,093 B2
APPLICATION NO. : 12/599397
DATED            : May 21, 2013
INVENTOR(S)      : Pierre-Marie Lemer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this
Eighth Day of September, 2015

Michelle K. Lee
*Director of the United States Patent and Trademark Office*